(12) United States Patent
Ueda et al.

(10) Patent No.: US 11,435,334 B2
(45) Date of Patent: Sep. 6, 2022

(54) DEVICE, PROGRAM, AND METHOD FOR DETERMINING NUMBER OF SAMPLES REQUIRED FOR MEASUREMENT, AND DEVICE, PROGRAM AND METHOD FOR ESTIMATING MEASUREMENT ACCURACY

(71) Applicant: NATIONAL INSTITUTE OF ADVANCED INDUSTRIAL SCIENCE AND TECHNOLOGY, Tokyo (JP)

(72) Inventors: Takao Ueda, Ibaraki (JP); Tatsuya Oki, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 117 days.

(21) Appl. No.: 16/617,398

(22) PCT Filed: Jun. 25, 2018

(86) PCT No.: PCT/JP2018/024067
§ 371 (c)(1),
(2) Date: Oct. 9, 2020

(87) PCT Pub. No.: WO2019/069512
PCT Pub. Date: Apr. 11, 2019

(65) Prior Publication Data
US 2021/0025864 A1   Jan. 28, 2021

(30) Foreign Application Priority Data

Oct. 5, 2017   (JP) .............................. JP2017-194812

(51) Int. Cl.
*G01N 33/24* (2006.01)
*G06F 17/18* (2006.01)
*G06K 9/62* (2022.01)

(52) U.S. Cl.
CPC ............. *G01N 33/24* (2013.01); *G06F 17/18* (2013.01); *G06K 9/6277* (2013.01)

(58) Field of Classification Search
CPC ....... G01N 33/24; G06F 17/18; G06K 9/6277
See application file for complete search history.

(56) References Cited

U.S. PATENT DOCUMENTS

2009/0069194 A1\* 3/2009 Ramakrishnan ..... C12Q 1/6869
                                                              506/9
2012/0221272 A1\* 8/2012 Ueno ................. G01R 31/2894
                                                             702/81

OTHER PUBLICATIONS

C.L. Evans et al., "Estimating error in measurements of mineral grain size distribution", Minerals Engineering, Oct. 2013, pp. 198-203, vol. 52, DOI: 10.1016/j.mineng.2013.09.005, Elsevier Ltd.
(Continued)

*Primary Examiner* — Bryan Bui
(74) *Attorney, Agent, or Firm* — Michael Best & Friedrich LLP

(57) ABSTRACT

To give reliability to statistical data on samples as discrete materials, a required sample-number determination device includes: a required sample number for each class acquisition unit configured to acquire a required sample number for each class $N_i$ by the following Equation (1) based on a proportion $P^\wedge_i$, that is a ratio of the number of samples in each class to the number of the samples in the population; a temporary required sample number acquisition unit configured to acquire a temporary required sample number $N_r$, which may be a maximum value among the required sample numbers for each class $N_i$; and a required sample number
(Continued)

determination unit configured to determine the temporary required sample number $N_r$ as a true required sample number when the sample number reaches the temporary required sample number $N_r$ or more,

[Mathematical 1]

$$N_i = \left(\frac{K_P}{\xi_i}\right)^2 \hat{P}_i(1 - \hat{P}_i) \quad (1)$$

in Equation (1), $\xi_i$ denotes a constant for accuracy that is set for each class, $K_P$ is a constant depending on set reliability, and i as indices denotes a class number assigned to each class.

5 Claims, 11 Drawing Sheets

(56) References Cited

OTHER PUBLICATIONS

Takao Ueda et al., "Statistical effect of sampling particle number on mineral liberation assessment", Minerals Engineering, Aug. 2016, pp. 204-212, vol. 98, DOI: 10.1016/j.mineng.2016.08.026, Elsevier Ltd.

S.L. Gay et al., "Using Two Dimensional Sectional Distributions to Infer Three Dimensional Volumetric Distributions—Validation using Temography", Particle & Particle Systems Characterization, Oct. 23, 2006, pp. 246-253, vol. 23, DOI: 10.1002/ppsc.200601056, Wiley-VCH Verlag GmbH & Co. KGaA.

International Search Report issued in Application No. PCT/JP2018/024067, dated Sep. 18, 2018.

* cited by examiner

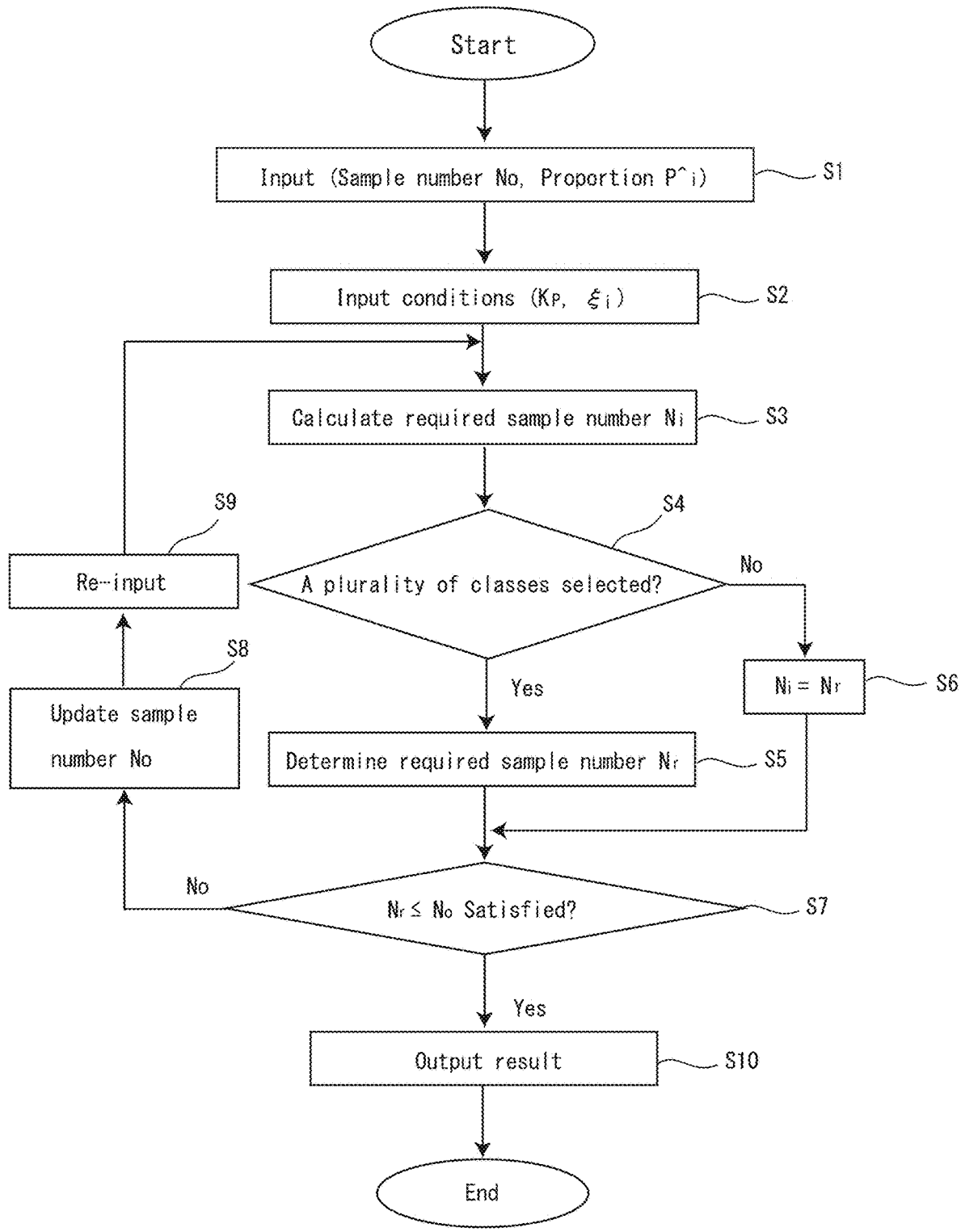

FIG.3

| Class i | Degree of locking | Proportion $P^i$ |
|---|---|---|
| 1 | 0.0 | xx |
| 2 | 0.0-0.1 | xx |
| 3 | 0.1-0.2 | xx |
| 4 | 0.2-0.3 | xx |
| 5 | 0.3-0.4 | xx |
| 6 | 0.4-0.5 | xx |
| 7 | 0.5-0.6 | xx |
| 8 | 0.6-0.7 | xx |
| 9 | 0.7-0.8 | xx |
| 10 | 0.8-0.9 | xx |
| 11 | 0.9-1.0 | xx |
| 12 | 1.0 | xx |

FIG.4

| Case | Conditions for accuracy | Accuracy ($\xi_i$) |
|---|---|---|
| 1 | Setting accuracy ($\xi_i$) for all classes at 0.01 | $\xi_i = 0.01$ where $i = 1$-$12$ |
| 2 | Setting $\xi_i$ for the classes x≥0.8 (i≥10) at 0.01, because high-content part of component A is concerned | $\xi_i = \begin{cases} 0.01 & \text{where } i = 10\text{-}12 \\ \infty & \text{where } i = 1\text{-}9 \end{cases}$ |
| 3 | Setting $\xi_i$ for the classes x=0 and 1 (i=1 and 12) at 0.01, because liberation parts of component A and B are concerned | $\xi_i = \begin{cases} 0.01 & \text{where } i = 1 \text{ and } 12 \\ \infty & \text{where } i = 2\text{-}11 \end{cases}$ |

TABLE 1

| Particle type | Component size by Voronoi tessellation ($F_S$) | Component content by Voronoi tessellation ($F_V$) |
|---|---|---|
| A | 0.54 | 0.5 |
| B | 0.54 | 0.1 |

FIG. 10

TABLE 2

| Case | Case 1 | | Case 2 | | Case 3 | |
|---|---|---|---|---|---|---|
| Embodiment | 1-1 | 1-1 | 1-1 | 1-1 | 1-1 | 1-1 |
| Liberation distribution | 2D (number) | 3D (number) | 2D (number) | 3D (number) | 2D (number) | 3D (number) |
| $N_r$ | 4642 | 6861 | 2475 | 876 | 844 | 100(0) |
| 1 | 100.0 | 100.0 | 100.0 | 100.0 | 96.3 | 100.0 |
| 2 | 99.9 | 100.0 | 100.0 | 100.0 | 100.0 | 100.0 |
| 3 | 99.1 | 100.0 | 100.0 | 100.0 | 100.0 | 100.0 |
| 4 | 97.2 | 99.9 | 100.0 | 100.0 | 100.0 | 100.0 |
| 5 | 96.5 | 97.0 | 100.0 | 100.0 | 100.0 | 100.0 |
| 6 | 94.5 | 94.5 | 100.0 | 100.0 | 100.0 | 100.0 |
| 7 | 95.4 | 94.3 | 100.0 | 100.0 | 100.0 | 100.0 |
| 8 | 95.4 | 97.5 | 100.0 | 100.0 | 100.0 | 100.0 |
| 9 | 98.0 | 99.3 | 100.0 | 100.0 | 100.0 | 100.0 |
| 10 | 99.5 | 100.0 | 95.2 | 95.6 | 100.0 | 100.0 |
| 11 | 99.9 | 100.0 | 98.2 | 100.0 | 100.0 | 100.0 |
| 12 | 100.0 | 100.0 | 99.7 | 100.0 | 96.1 | 100.0 |
| Minimum value | 94.5 | 94.3 | 95.2 | 95.6 | 96.1 | 100.0 |

FIG. 11

TABLE 3

| Case | Case 1 | |
|---|---|---|
| Embodiment | 1-1 | 1-2 |
| Liberation distribution | 2D (area) | 2D (area) |
| $N_r$ | 5091 | 6164 |
| 1 | 100.0 | 100.0 |
| 2 | 100.0 | 100.0 |
| 3 | 98.8 | 99.8 |
| 4 | 96.8 | 98.1 |
| 5 | 94.1 | 96.4 |
| 6 | 92.8 | 94.9 |
| 7 | 91.7 | 94.9 |
| 8 | 93.9 | 96.1 |
| 9 | 96.7 | 98.0 |
| 10 | 99.4 | 99.6 |
| 11 | 100.0 | 100.0 |
| 12 | 100.0 | 100.0 |
| Minimum value | 91.7 | 94.9 |

FIG. 12

TABLE 4

| Case | Case 1 | | Case 2 | | Case 3 | |
|---|---|---|---|---|---|---|
| Embodiment | 1-1 | 1-1 | 1-1 | 1-1 | 1-1 | 1-1 |
| Liberation distribution | 2D (number) | 3D (number) | 2D (number) | 3D (number) | 2D (number) | 3D (number) |
| $N_r$ | 9220 | 9579 | 100(88) | 100(0) | 9220 | 2107 |
| 1 | 94.0 | 100.0 | 100.0 | 100.0 | 95.7 | 94.0 |
| 2 | 97.0 | 94.5 | 100.0 | 100.0 | 100.0 | 100.0 |
| 3 | 99.5 | 96.6 | 100.0 | 100.0 | 100.0 | 100.0 |
| 4 | 99.8 | 99.8 | 100.0 | 100.0 | 100.0 | 100.0 |
| 5 | 100.0 | 100.0 | 100.0 | 100.0 | 100.0 | 100.0 |
| 6 | 100.0 | 100.0 | 100.0 | 100.0 | 100.0 | 100.0 |
| 7 | 100.0 | 100.0 | 100.0 | 100.0 | 100.0 | 100.0 |
| 8 | 100.0 | 100.0 | 100.0 | 100.0 | 100.0 | 100.0 |
| 9 | 100.0 | 100.0 | 100.0 | 100.0 | 100.0 | 100.0 |
| 10 | 100.0 | 100.0 | 98.0 | 100.0 | 100.0 | 100.0 |
| 11 | 100.0 | 100.0 | 99.0 | 100.0 | 100.0 | 100.0 |
| 12 | 100.0 | 100.0 | 98.9 | 100.0 | 100.0 | 100.0 |
| Minimum value | 94.0 | 94.5 | 98.0 | 100.0 | 95.7 | 94.0 |

FIG. 13

TABLE 5

| Case | Case 1 | |
|---|---|---|
| Embodiment | 1-1 | 1-2 |
| Liberation distribution | 2D (area) | 2D (area) |
| $N_r$ | 8617 | 9602 |
| 1 | 92.7 | 94.4 |
| 2 | 93.2 | 94.6 |
| 3 | 97.1 | 98.1 |
| 4 | 99.2 | 99.7 |
| 5 | 100.0 | 100.0 |
| 6 | 100.0 | 100.0 |
| 7 | 100.0 | 100.0 |
| 8 | 100.0 | 100.0 |
| 9 | 100.0 | 100.0 |
| 10 | 100.0 | 100.0 |
| 11 | 100.0 | 100.0 |
| 12 | 100.0 | 100.0 |
| Minimum value | 92.7 | 94.4 |

FIG. 14

DEVICE, PROGRAM, AND METHOD FOR DETERMINING NUMBER OF SAMPLES REQUIRED FOR MEASUREMENT, AND DEVICE, PROGRAM AND METHOD FOR ESTIMATING MEASUREMENT ACCURACY

TECHNICAL FIELD

The present invention relates to devices, programs, and methods for determining the number of samples required for measurement that determine the required number of samples as a certain number of discrete materials belonging to the population so as to give the reliability to the statistical data based on the measurement result of a physical amount on the discrete materials. The present invention also relates to devices, programs and methods for estimating measurement accuracy to evaluate the reliability of the statistical data of the actually measured physical amount.

BACKGROUND ART

For beneficiation of natural ores, some physical amounts of the comminuted ore particles are measured, which include the liberation distribution and the degree of liberation. Specifically for a group of ore particles made up of one or a plurality of components, the ore particles are divided into classes each having different content ratio of the component-of-interest, and the liberation distribution indicates the existence ratio of each class in the form of cumulative distribution. The degree of liberation indicates the existence ratio of the ore particles made up of one component in the group. To measure these physical amounts, the ore particles are mounted in resin as a sample, and sections of the sample are analyzed with an analyzer to create a series of statistical data of the physical amounts.

To obtain reliable statistical data on the physical amounts, such a data-creation procedure may be conducted for all of the ore particles belonging to the group, i.e., the population.

This procedure for all of the ore particles belonging to the population, however, is impractical because the procedure to create the statistical data requires a lot of money and time.

For a more practical approach, Non-Patent Document 1 proposes a bootstrap method to obtain the liberation distribution of the ore particles. The method measures several hundreds of samples belonging to the group of the ore particles to create a sample database, and then extracts a certain number of samples repeatedly from the sample database to examine the variation. The method then conducts fitting of the variation to estimate the equation representing the relationship between the number of the samples and the variation.

Such a proposed method, however, will have an error depending on the types of functions used for the fitting or the number of data for the fitting. There is no means to predict the magnitude of this error. The method, which is able to estimate the statistical reliability of the statistical data, is not able to predict the magnitude of an error included in the data, and may not ensure the reliability of the estimated result.

Non-Patent Document 2 proposes a method to obtain the degree of liberation for ore particles. To this end, this method estimates the relationship between the number of measurement samples and the confidence interval based on the interval-estimation technique for the population proportion.

This proposal, however, is targeted at the degree of liberation only, and is not applicable to the liberation distribution. Although both of the degree of liberation and the liberation distribution are indices relating to the content ratio of the component-of-interest, the index required by a user to beneficiate natural ores may vary with the types of the natural ores, their producing regions, and the like. Both of these indices therefore are required to have high reliability of the statistical data depending on the user's needs.

Beneficiation of natural ores may require high accuracy for only a part of the liberation distribution (e.g., 90% or higher of the content ratio of a specific component). In this case, a less number of measurement samples suffices than in the case of ensuring high accuracy for the overall liberation distribution, and this needs another method to determine the number of samples required for measurement targeted to a part of the liberation distribution. There is currently no method available for that case.

There is also no method to estimate the accuracy of the already created statistical data. Users therefore are not able to evaluate the reliability of the statistical data correctly.

Such problems may arise not only in the scene for ore particles of the natural ores as stated above but also in any scene for discrete materials, such as dealing with waste materials for recycling. Similar problems will arise for the method of measuring other scales of the physical amounts, such as the area, the volume, the weight and the density, instead of the liberation distribution (and the degree of liberation), because such a method also needs to decrease the number of samples required for measurement as well as the technique to evaluate the reliability of the already measured statistical data.

PRIOR ART DOCUMENTS

Non-Patent Documents

Non-Patent Document 1: Evans, C. L., Napier-Munn, T. J., 2013. Estimating error in measurements of mineral grain size distribution. Miner. Eng. 52, 198-203. doi: 10.1016/j.mineng. 2013.09.005

Non-Patent Document 2: Ueda, T., Oki, T., Koyanaka, S., 2016. Statistical effect of sampling particle number on mineral liberation assessment. Miner. Eng. 98, 204-212. doi: 10.1016/j.mineng. 2016.08.026

SUMMARY OF THE INVENTION

Problems to be Solved by the Invention

The present invention aims to solve the above-stated problems and provide a device, a program, and a method for determining the number of samples required for measurement to give the reliability to the statistical data of samples as discrete materials as well as a device, a program and a method for estimating measurement accuracy.

Means for Solving the Problems

Means for solving the above-stated problems is as follows.

<1> A required sample-number determination device includes: a required sample number for each class acquisition unit configured to, when samples of a population made up of a plurality of discrete materials are divided into a plurality of classes based on differences in a physical amount, acquire a required sample number for each class $N_i$ of selected classes that are all or a part of the classes by the following Equation (1) based on a proportion $P^\wedge_i$, that is a ratio of the number of samples in each class to the number of the samples in the population;

a temporary required sample number acquisition unit configured to acquire a temporary required sample number $N_r$, when a plurality of classes are selected as the selected classes, the temporary required sample number $N_r$ being a maximum value among the required sample numbers for each class $N_i$ of the selected classes, and when a single class is selected as the selected class, the temporary required sample number $N_r$ being the required sample number for each class $N_i$ of the selected class; and a required sample number determination unit configured to, in the relationship between a sample number determined at one processing by the required sample number for each class acquisition unit and the temporary required sample number acquisition unit and the temporary required sample number $N_r$, if the sample number falls below the temporary required sample number $N_r$, update the sample number to be the temporary required sample number $N_r$ or more and make the required sample number for each class acquisition unit and the temporary required sample number acquisition unit repeatedly execute the acquisition of the required sample number for each class $N_i$ and the temporary required sample number $N_r$ so as to determine the temporary required sample number $N_r$ as a true required sample number when the sample number reaches the temporary required sample number $N_r$ or more,

[Mathematical 1]

$$N_i = \left(\frac{K_P}{\xi_i}\right)^2 \hat{P}_i(1 - \hat{P}_i) \quad (1)$$

in Equation (1), $\xi_i$ denotes a constant for accuracy that is set for each class, $K_P$ is a constant depending on reliability, which is set as probability satisfying the relationship of $\hat{P}_i - \xi_i < P_i < \hat{P}_i + \xi_i$, where $P_i$ denotes the proportion that is a ratio of the number of the discrete materials in each class to all of the discrete materials of the population, and i as indices denotes a class number assigned to each class.

<2> The required sample-number determination device according to <1>, wherein the discrete materials are multicomponent particles, and the physical amount is a liberation distribution of the multicomponent particles.

<3> The required sample-number determination device according to <2>, wherein the physical amount is a liberation distribution and cross-sectional areas of the multicomponent particles, and the required sample-number determination device sets classes based on differences in the cross-sectional area and divides the classes into sub-classes based on differences in the liberation distribution, or sets classes based on differences in the liberation distribution and divides the classes into sub-classes based on differences in the cross-sectional area, and calculates a required sample number with a proportion $\hat{P}_i^j$ that is a ratio of the number of the samples of each class to the number of samples belonging to each sub-class, instead of the proportion $\hat{P}_i$, where i as the index in the proportion $\hat{P}_i^j$ denotes the class number assigned to each class, and j denotes the sub-class number assigned to each sub-class.

<4> A required sample-number determination program that makes a computer function as the required sample-number determination device according to any one of <1> to <3>,

[Mathematical 2]

$$N_i = \left(\frac{K_P}{\xi_i}\right)^2 \hat{P}_i(1 - \hat{P}_i) \quad (1)$$

in Equation (1), $\xi_i$ denotes a constant for accuracy that is set for each class, $K_P$ is a constant depending on reliability, which is set as probability satisfying the relationship of $\hat{P}_i - \xi_i < P_i < \hat{P}_i + \xi_i$, where $P_i$ denotes the proportion that is a ratio of the number of the discrete materials in each class to all of the discrete materials of the population, and i as indices denotes a class number assigned to each class.

<5> A method for determining a required sample number includes:

a required sample number for each class acquisition step of, when samples of a population made up of a plurality of discrete materials are divided into a plurality of classes based on differences in a physical amount, acquiring a required sample number for each class $N_i$ of selected classes that are all or a part of the classes by Equation (1) based on a proportion $\hat{P}_i$ that is a ratio of the number of samples in each class to the number of the samples in the population;

a temporary required sample number acquisition step of acquiring a temporary required sample number $N_r$, when a plurality of classes are selected as the selected class, the temporary required sample number $N_r$ being a maximum value among the required sample numbers for each class $N_i$ of the selected classes, and when a single class is selected as the selected class, the temporary required sample number $N_r$ being the required sample number for each class $N_i$ of the selected class; and a required sample number determination step of, in the relationship between a sample number determined at one processing by the required sample number for each class acquisition step and the temporary required sample number acquisition step and the temporary required sample number $N_r$, if the sample number falls below the temporary required sample number $N_r$, updating the sample number to be the temporary required sample number $N_r$ or more and repeatedly conducting the required sample number for each class acquisition step and the temporary required sample number acquisition step so as to determine the temporary required sample number $N_r$ as a true required sample number when the sample number reaches the temporary required sample number $N_r$ or more,

[Mathematical 3]

$$N_i = \left(\frac{K_P}{\xi_i}\right)^2 \hat{P}_i(1 - \hat{P}_i) \quad (1)$$

in Equation (1), $\xi_i$ denotes a constant for accuracy that is set for each class, $K_P$ is a constant depending on reliability, which is set as probability satisfying the relationship of $\hat{P}_i - \xi_i < P_i < \hat{P}_i + \xi_i$, where $P_i$ denotes the proportion that is a ratio of the number of the discrete materials in each class to all of the discrete materials of the population, and i as indices denotes a class number assigned to each class.

<6> A measurement-accuracy estimation device includes an accuracy estimation unit configured to, when samples of a population made up of a plurality of discrete materials are divided into a plurality of classes based on differences in a physical amount, solve the following Equation (1) about accuracy $\xi_i$ based on proportion $\hat{P}_i$ that is a ratio of the number of samples in each class to the number of the samples in the population, and the actually measured sample number $N_i$ for each class,

[Mathematical 4]

$$N_i = \left(\frac{K_P}{\xi_i}\right)^2 \hat{P}_i(1-\hat{P}_i) \quad (1)$$

in Equation (1), $\xi_i$ denotes a value of the accuracy for each class, $K_P$ is a constant depending on reliability, which is set as probability satisfying the relationship of $P\hat{}_i-\xi_i<P_i<P\hat{}_i+\xi_i$, where $P_i$ denotes the proportion that is a ratio of the number of the discrete materials in each class to all of the discrete materials of the population, and i as indices denotes a class number assigned to each class.

<7> A measurement-accuracy estimation program that makes a computer function as the measurement-accuracy estimation device according to <6>.

<8> A method for estimating measurement accuracy includes an accuracy estimation step of, when samples of a population made up of a plurality of discrete materials are divided into a plurality of classes based on differences in a physical amount, solving the following Equation (1) about accuracy $\xi_i$ based on proportion $P\hat{}_i$ that is a ratio of the number of samples in each class to the number of the samples in the population, and the actually measured sample number $N_i$ for each class,

[Mathematical 5]

$$N_i = \left(\frac{K_P}{\xi_i}\right)^2 \hat{P}_i(1-\hat{P}_i) \quad (1)$$

in Equation (1), $\xi_i$ denotes a value of the accuracy for each class, $K_P$ is a constant depending on reliability, which is set as probability satisfying the relationship of $P\hat{}_i-\xi_i<P_i<P\hat{}_i+\xi_i$, where $P_i$ denotes the proportion that is a ratio of the number of the discrete materials in each class to all of the discrete materials of the population, and i as indices denotes a class number assigned to each class.

Advantageous Effect of the Invention

The present invention solves the problems as stated above and provides a device, a program, and a method for determining the number of samples required for measurement to give the reliability to the statistical data of samples as discrete materials as well as a device, a program and a method for estimating measurement accuracy.

BRIEF DESCRIPTION OF THE DRAWINGS

FIG. 2 is a flowchart to describe the operation of the required sample-number determination device.

FIG. 3 shows an example of the input information.

FIG. 4 shows an example of the conditions set for accuracy at Step S3.

FIG. 9(*b*) shows a cross section of the particle type B;

FIG. 10 is Table 1, which shows two types of setting values for $F_S$ and $F_V$ (particle type A and particle type B).

FIG. 11 is Table 2, which shows the required sample number for measurement $N_r$ and the percentage of correct answers R, which shows the verification result by the required sample-number determination device 1 according to Embodiment 1-1 for the particle type A, 3D(number) and 2D(number).

FIG. 12 is Table 3, which shows $\xi_i$, the required number of samples for measurement $N_r$ for the set condition and the percentage of correct answers R for Case 1 using these devices.

FIG. 13 is Table 4, which shows $\xi_i$, the required number of samples for measurement $N_r$ for the set condition and the percentage of correct answers R for Case 1.

FIG. 14 is Table 5, which shows $\xi_i$, the required number of samples for measurement $N_r$ for the set condition and the percentage of correct answers R for Case 1 using these devices.

MODE FOR CARRYING OUT THE INVENTION

Figure 1:
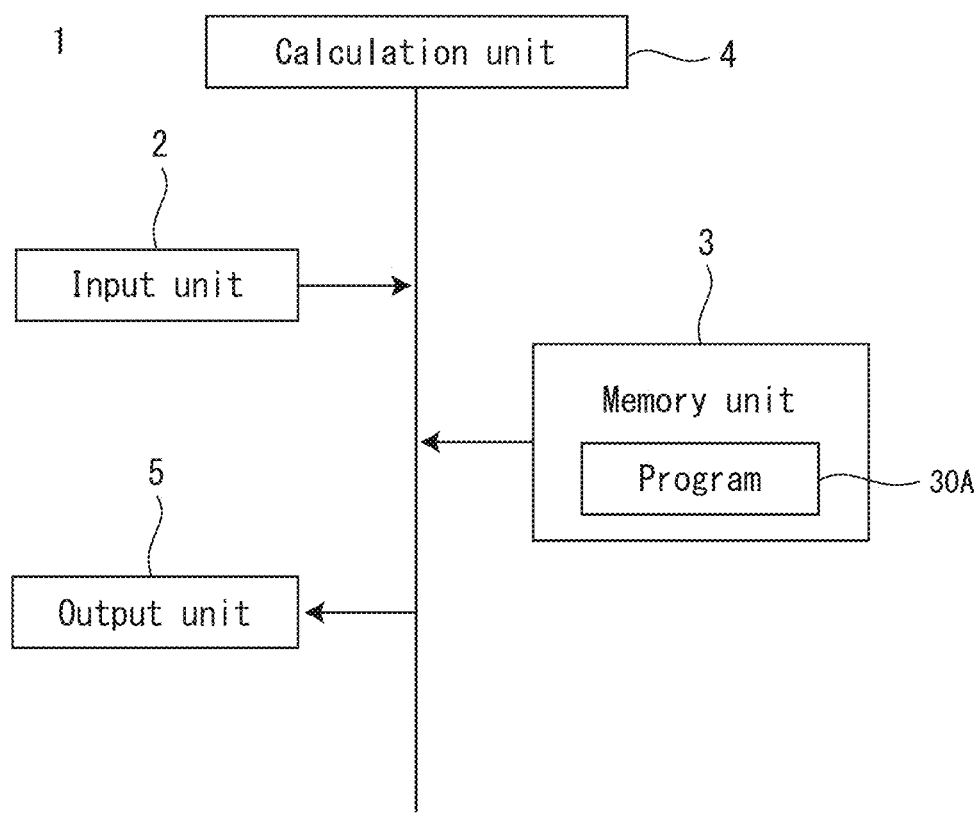
FIG. 1 is a block diagram showing the configuration of a required sample-number determination device according to Embodiment 1-1.

Firstly the following describes interval estimation of the population proportion in the context of the present invention. The interval estimation of the population proportion estimates the proportion of a physical amount of a population representative of the feature of the population. When the population is made up of a sufficient number of samples, the population proportion can be estimated with certain accuracy by randomly extracting a certain number of samples from the population, obtaining the proportion of the physical amount of the samples, and then approximating a displacement between the sample proportion and the population proportion with normal distribution.

In order to represent the population proportion (P) with certain accuracy (±$\xi$), i.e., to be $P\hat{}-\xi<P<P\hat{}+\xi$, the required number (N) of samples having the proportion ($P\hat{}$) is represented by the following Equation (A):

[Mathematical 6]

$$N_i = \left(\frac{K_P}{\xi}\right)^2 \hat{P}(1-\hat{P}) \quad (A)$$

where $K_P$ in Equation (A) denotes a constant depending on the set reliability (the probability to be $P\hat{}-\xi<P<P\hat{}+\xi$). For example, this gives $K_P=1.96$ for the reliability of 95%.

The present invention includes roughly two embodiments. That is, Embodiment 1 calculates the number ($N_r$) of samples required for measurement so as to satisfy the required accuracy ($\xi_i$) that is determined before the measurement. Embodiment 2 estimates the accuracy ($\xi_i$) of the statistical data on a physical amount, where the physical amount is already measured and the number of the measured samples (particles) also is known.

The population is made up of a plurality of discrete materials.

The discrete materials mean materials that are distinguishable from the outside space. Examples of the discrete materials include particles, block objects, crystals, cells, and bubbles, and the discrete materials of the same type constitute one population.

The physical amount can be any physical amount specific to the discrete materials or a section of the discrete materials. Examples of the physical amount include the volume, surface area, cross-sectional area, axial length, perimeter, component content ratio (the liberation distribution or the degree of liberation as stated above), density, magnetic property, conductivity, surface-area percentage of the components (the percentage of a component occupying the surface area), and aspect ratio (ratio between the maximum axial length and the minimum axial length orthogonal to the maximum axial length).

For ease of explanation, the following describes an example where the samples, i.e., the discrete materials, making up the population are multicomponent particles, such as ore particles and waste material for recycling, and the physical amount is the liberation distribution.

For a group of the multicomponent particles made up of one or a plurality of components, the multicomponent particles are divided into classes each having different content ratio of the component-of-interest, and the liberation distribution then indicates the existence ratio of each class in the form of cumulative distribution. The field of beneficiation typically divides the ratio x of the component-of-interest into 12 classes (i.e., 0.0, more than 0.0 and 0.1 or less (0.0 to 0.1), more than 0.1 and 0.2 or less (0.1 to 0.2), . . . more than 0.9 and less than 1.0 (0.9 to 1.0), and 1.0), and this example follows this classification. $P_i$ denotes the proportion of class i.

When the liberation distribution is obtained through the observation of a two-dimensional sectional image of the multicomponent particles, the liberation distribution is typically calculated based on the number of particles or based on the area.

Number-based $P_i$ based on the number of particles is typically calculated by the following Equation: $P_i=M_i/M_{all}$, where $M_i$ denotes the number of particle sections in class i and $M_{all}$ denotes the total number of particle sections.

Areal-based $P_i$ based on the area is typically calculated by the following Equation: $P_i=S_i/S_{all}$, where $S_i$ denotes the sum of sectional areas of the particles in class i and $S_{all}$ denotes the sum of the sectional areas of all particles.

While the number-based liberation distribution evaluates the existence ratio of particles equally irrespective of the cross-sectional area of the particles, the areal-based liberation distribution evaluates the existence ratio of a particle section having a larger cross-sectional area more and evaluates the existence ratio of a particle section having a smaller cross-sectional area less. The multicomponent particles have a structural feature that only one component is likely observed from a small particle section, and is unlikely observed from a large particle section as compared with a small particle section. In other words, the liberation distribution in a section of the multicomponent particles depends on the size of the cross-sectional area of the particles.

The interval estimation of the population proportion assumes that each sample has an equal weight, and simple interval estimation of the population portion for the liberation distribution based on the area therefore will degrade the measurement accuracy. One aspect of the present invention therefore gives the reliability to statistical data based on the number of samples while partially incorporating the concept based on the area. This is described in details with reference to the method for setting sub-classes described later.

Embodiment 1 includes the following two embodiments. Specifically Embodiment 1 includes two embodiments of; Embodiment 1-1 where the samples have an equal weight; and Embodiment 1-2 where each sample has a different weight.

For the liberation distribution of the multicomponent particles as one example, a preferable embodiment will be different by the way of considering the liberation distribution.

For example, when a two-dimensional cross section of the multicomponent particles is observed and the liberation distribution is measured two dimensionally based on the number of particles (2D(number)), the samples have the same weight. This case therefore corresponds to Embodiment 1-1.

When a two-dimensional cross section of the multicomponent particles is observed and the liberation distribution is measured two dimensionally while considering a difference in cross-sectional area (2D(area)), the samples have different weights. This case therefore corresponds to Embodiment 1-2.

When the liberation distribution is measured three dimensionally based on the number of particles, the samples have the same weight. The liberation distribution based on the number of particles (3D(number)) therefore corresponds to Embodiment 1-1.

Considering these points, the following describes Embodiment 1 (Embodiment 1-1, Embodiment 1-2) and Embodiment 2 of the present invention.

Embodiment 1-1

Referring to FIG. 1, the following describes the configuration of Embodiment 1-1 of the present invention. Embodiment 1-1 relates to one embodiment of a device for determining the number of samples required for measurement of the present invention. FIG. 1 is a block diagram showing the configuration of the device for determining the number of samples required for measurement (hereinafter called a required sample-number determination device) according to Embodiment 1-1.

The required sample-number determination device 1 is an information processing device configured to determine the minimum required sample number for measurement of discrete materials that is required for the estimation of the population proportion with a target accuracy $\xi_i$. As shown in FIG. 1, this device includes an input unit 2, a memory unit 3, a calculation unit 4, and an output unit 5.

The input unit 2 includes well-known information input means, such as for key inputting, touch inputting, or a data reader, and is configured to output the input information to the calculation unit 4.

The memory unit 3 includes a well-known memory, such as RAM (Random Access Memory) or a ROM (Read Only Memory), and is configured to store various types of programs and data, and function as a workspace of the calculation unit 4 as well.

The memory unit 3 of the present embodiment stores a program 30A.

The program 30A is a program for determining the required sample number for measurement, and is executable by the calculation unit 4. The program 30A will be described later.

The calculation unit 4 includes a well-known calculation means, such as a CPU (Central Processing Unit), and is configured to execute the processing according to a predetermined program based on input instructions, and issue instructions to various parts to control the required sample-number determination device 1 in a centralized manner.

Specifically the calculation unit 4 reads a predetermined program from the memory unit 3 in accordance with data and instructions from the input unit 2, and executes the corresponding processing. The calculation unit 4 also stores the result of the processing in the memory unit 3 and outputs the result to the output unit 5.

Referring to FIG. 2, the following describes the operation of the required sample-number determination device 1 and the program 30A that is the program for determining the required sample number for measurement. FIG. 2 is a flowchart to describe the operation of the required sample-number determination device.

Firstly the calculation unit 4 receives information from the input unit 2 (Step S1).

When the samples of the population made up of a plurality of discrete materials are divided into a plurality of classes based on differences in the physical amount, the input information contains the proportion $\hat{P}_i$ that is the ratio of the number of the samples in each class and the number of the samples $N_0$.

For instance, when the discrete materials are the multicomponent particles and the physical amount is the liberation distribution, then the input information has the form shown in FIG. 3. FIG. 3 shows an example of the input information.

The number of samples $N_0$ required to create the input information is a relatively small number because a too large number will be a waste corresponding to the amount exceeding the number required for the measurement determined by the required sample-number determination device 1. The number of samples preferably increases at the timing for updating described later.

Next the calculation unit 4 receives conditions (input) from the input unit 2 (Step S2).

The conditions include $\xi_i$, $K_P$, and selected classes as needed.

$\xi_i$ is a constant of accuracy that is set for each class. A smaller value for $\xi_i$ (e.g., 0.01 to 0.1) indicates higher accuracy, and a larger value indicates lower accuracy.

$K_P$ is a constant depending on the reliability, which is set as the probability satisfying the relationship of $\hat{P}_i - \xi_i < P_i < \hat{P}_i + \xi_i$, where $P_i$ denotes the proportion that is the ratio of the number of the discrete materials in each class to all of the discrete materials of the population. In one example, the reliability of 90% gives $K_P$=1.65, the reliability of 95% gives $K_P$=1.96, and the reliability of 99% gives $K_P$=2.58. That is, $K_P$ can be a value from 1.65 to 2.58 for the reliability set in the range of 90% to 99% (see Reference 1 described below).

The selected classes are all of the classes or a part of the classes that are selected. Examples of the case to select a part of the classes include the situation where the information on class 1 and class 12, which indicates that the particles are made up of a single component, i.e., liberation particles, is considered as especially important information among the 12 classes shown in FIG. 3. Such setting of the selected classes tends to require a less number of the samples for measurement than the case of ensuring high accuracy for all of 12 classes, because high accuracy is required only for class 1 and class 12 and other classes do not relate to the processing to determine the number of the samples required for measurement.

Reference 1: Miki WADACHI, Kiyoshi SOGO "Key point Probability Statistics" Iwanami-shoten in Japan (1993)

Next the calculation unit 4 reads the program 30A from the memory unit 3, and executes the following processing in accordance with the program 30A.

Firstly the calculation unit 4 acquires the required sample number for each class $N_i$ based on the input information and the information on the conditions and through the calculation by the following Equation (1). The calculation unit 4 acquires $N_i$ for all of the selected classes (Step S3).

[Mathematical 7]

$$N_i = \left(\frac{K_P}{\xi_i}\right)^2 \hat{P}_i(1 - \hat{P}_i) \tag{1}$$

When a plurality of classes are selected as the selected class, e.g., when the selected classes include two classes of class 1 and class 12 or all of the 12 classes in FIG. 3, the calculation unit 4 sets a temporary required sample number $N_r$ to ensure the accuracy $\xi_i$ for all of the selected classes so that the temporary required sample number $N_r$ is the maximum value among all of the required sample numbers for each class $N_i$ (Steps S4, S5).

When a single class is selected as the selected class, the calculation unit 4 sets the required sample number for each class $N_i$ of the selected class as a temporary required sample number $N_r$ (Steps S4, S6).

Note here that the processing at Steps S2 to S6 can be simplified as follows.

Specifically the simplified processing omits the setting of the selected class(es) at Step S2, and calculates the required sample number $N_i$ for all of the classes divided based on the physical amount at Step S3. The simplified processing then sets ∞ as $\xi_i$ in the above Equation (1) for the non-selected classes to calculate the required sample number $N_i$ at Step S3 so that the required sample number for each class $N_i(=0)$ is ignorable and the selected class(es) only contributes to determine the temporary required sample number $N_r$ at Step S5.

Such simplified processing just sets ∞ as $\xi_i$ for the non-selected classes at Step S3 to omit the setting of the selected class(es) at Step S2 and the processing at Steps S4 and S5.

In one example, for the liberation distribution (12 classes in total) of the multicomponent particles shown in FIG. 3, the simplified processing just sets $\xi_i$ at Step S3 depending on the set accuracy including Cases 1 to 3 shown in FIG. 4 to conduct the processing common to all of Cases 1 to 3, and is able to omit the processing to set the selected class(es) at Step S2 and the processing at Steps S4, S5. FIG. 4 shows an example of the conditions set for accuracy at Step S3.

Next the calculation unit 4 compares the sample number $N_0$ with the temporary required sample number $N_r$ so as to determine whether the sample number $N_0$ and the temporary required sample number $N_r$ satisfy the relationship of $N_0 > N_r$ or not (Step S7).

If they do not satisfy the relationship of $N_0 > N_r$, the calculation unit 4 updates the sample number No to be the temporary required sample number $N_r$ or more (Step S8). The updated sample number $N_0$ can be the temporary required sample number $N_r$ or more to satisfy the updating condition, and a too large sample number will be a waste corresponding to the amount exceeding the required sample number determined by the required sample-number determination device 1. The updated sample number therefore is preferably the same as the temporary required sample number $N_r$.

The processing by the calculation unit 4 once shifts to the standby state. Then the user randomly extracts other discrete materials, which are different from the discrete materials as the target of the initial sample number $N_0$, from the population based on the updated sample number $N_0$ and measures the physical amount again.

When receiving the proportion $P\hat{}_i$ based on the result of the re-measurement and the re-input sample number $N_0$ after the updating (Step S9), the calculation unit 4 executes the processing from Step S3 based on the re-inputting and repeats the processing from Step S3 to Step S9 until the sample number $N_0$ and the temporary required sample number $N_r$, satisfy the relationship of $N_0 > N_r$.

That is, the calculation unit 4 is configured to, in the relationship between the sample number $N_0$ determined at one processing to acquire the required sample number for each class $N_i$ and the temporary required sample number $N_r$, and the temporary required sample number $N_r$, if the sample number $N_0$ falls below the temporary required sample number $N_r$, update the sample number $N_0$ to be the temporary required sample number $N_r$, or more and repeatedly execute the acquisition of the required sample number for each class $N_i$ and the temporary required sample number $N_r$.

Next when the sample number $N_0$ and the temporary required sample number $N_r$ satisfy the relationship of $N_0 > N_r$, the calculation unit 4 determines that this temporary required sample number $N_r$ is the true required sample number, and outputs the result of determination to the output unit 5.

If the temporary required sample number $N_r$ is the number of the samples in the population or higher, measurement with this updated sample number $N_0$ will fail. The calculation unit 4 therefore executes canceling processing (not shown) following end inputting, instead of Steps S7 to S10, and determines that the current temporary required sample number $N_r$ is the true required sample number and outputs the result of determination to the output unit 5.

The above-stated required sample-number determination device 1 ensures the set accuracy ($\xi$), and so gives the reliability to the statistical data of the samples as the discrete materials based on the final sample number $N_0$. This required sample-number determination device 1 determines the minimum required sample number while ensuring the set accuracy ($\xi$), and so remarkably reduces the number of the discrete materials to be measured.

Embodiment 1-2

Figure 5:
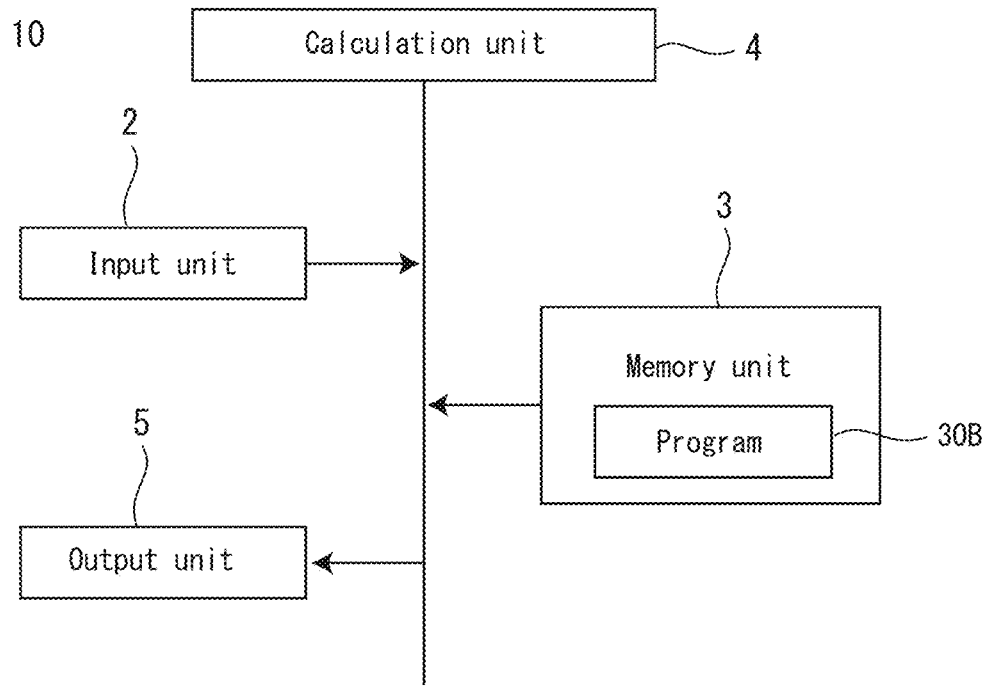
FIG. 5 is a block diagram showing the configuration of a required sample-number determination device according to Embodiment 1-2.

Referring to FIG. 5, the following describes the configuration of Embodiment 1-2 of the present invention. Embodiment 1-2 relates to one embodiment of a required sample-number determination device of the present invention. FIG. 5 is a block diagram showing the configuration of the required sample-number determination device according to Embodiment 1-2.

As shown in FIG. 5, the required sample-number determination device 10 stores a program 30B instead of the program 30A of the required sample-number determination device 1. The following describes the operation of the required sample-number determination device 10 in accordance with the program 30B. Since other configuration is similar to that of the required sample-number determination device 1, their descriptions are omitted.

Unlike the required sample-number determination device 1 dealing with the case where all of the samples have the same weight, the required sample-number determination device 10 deals with the case where the samples have different weights.

The following describes the case as an example where the physical amount is the liberation distribution of multicomponent particles and cross-sectional areas of the multicomponent particles. The required sample-number determination device 10 sets classes based on differences in the cross-sectional area and then divides the classes into sub-classes based on differences in the liberation distribution, or sets classes based on differences in the liberation distribution and then divides the classes into sub-classes based on differences in the cross-sectional area.

In one example, the number of the classes i is 12 in accordance with the liberation distribution (i in this example are integers from 1 to 12) and the number of the sub-classes ($n_{size}$) is 3, including large, medium, and small, in accordance with the difference in cross-sectional area. Then each of the 12 classes for the liberation distribution is subdivided into three sub-classes in accordance with the difference in cross-sectional area to be 36 classes in total.

This embodiment replaces the proportion $P\hat{}_i$ in Equation (1) as stated above with the proportion $P\hat{}_i^j$, where j denotes the number of the sub-classes (in this example j are integers from 1 to 3), and the proportion $P\hat{}_i^j$ is the ratio of the number of the samples of each class i to the number of the samples belonging to each sub-class.

Specifically 100 pieces of the multicomponent particles are used as the samples, and three sub-classes j are set for these samples including sub-class 1 (small), sub-class 2 (medium), and sub-class 3 (large) in accordance with their cross-sectional areas. Then the number of samples belonging to each sub-class j is counted. Let that the number of the samples belonging to sub-class 1 (small) is 20, the number of the samples belonging to sub-class 2 (medium) is 45, and the number of the samples belonging to sub-class 3 (large) is 35. Each sub-class j includes 12 classes i in accordance with the liberation distribution, and the ratio of the number of samples for each class i to the number of samples belonging to each sub-class j is calculated. For instance, when among the 20 samples belonging to sub-class 1 (small), the number of the samples belonging to the class having the ratio of the component-of-interest that is 0 (class i=1) is 8, $P\hat{}_i^j = P\hat{}_1^1 = 0.4$. When among the 20 samples belonging to sub-class 1 (small), the number of the samples belonging to the class having the ratio of the component-of-interest that is 1.0 (class i=12) is 10, $P\hat{}_i^j = P\hat{}_{12}^1 = 0.5$. In this way, $P\hat{}_i^j$ is calculated for each of the sub-divided 36 sub-classes of the classes i. Note here that $P\hat{}_i^j$ is not the ratio of the number of the samples belonging to each of the classes (36 classes in total) with respect to the number of all of the samples in total, and is the ratio of the number of the samples belonging to each of the classes (36 classes in total) with respect to the number of the samples belonging to the sub-class, which means that $\Sigma_i P\hat{}_i^j = 1$. That is, $\Sigma_i P\hat{}_i^1 = 1$, $\Sigma_i P\hat{}_i^2 = 1$, and $\Sigma_i P\hat{}_i^3 = 1$.

The proportion $P\hat{}_i^j$ instead of the proportion $P\hat{}_i$ in the above Equation (1) reduces adverse effects from different weights of the samples.
The following describes the reasons.

When a cross-sectional image is obtained near the end of a multicomponent particle having a plurality of components, for example, only one component is likely to be observed from such a part having a small cross-sectional area. This leads to the evaluation that the proportion $P^\wedge_i$ of classes 1 and 12 tends to be large. When the part has a large cross-sectional area, this leads to the evaluation that the proportion $P^\wedge_i$ of classes 2 to 11 tends to be large.

"$P^\wedge_i(1-P^\wedge_i)$" in Equation (1) has the maximum value when the proportion $P^\wedge_i$ is 0.5, and decreases with the proximity of the proportion $P^\wedge_i$ to 0 or 1. The required sample number for each class $N_i$ increases with the value of "$P^\wedge_i(1-P^\wedge_i)$" and such a required sample number for each class is likely to be selected as the temporary required sample number $N_r$. This means that the way of estimating a cross-sectional area affects which one of the classes has the proportion $P^\wedge_i$ closer to 0.5, and so affects the determination of the required number of samples.

Note here that the liberation distribution may be determined based on the areal-base concept unlike the present invention based on the number-base concept.

When the liberation distribution is evaluated based on the areal-base method, the existence ratio of a particle section having a large cross-sectional area is evaluated more, and the existence ratio of a particle section having a smaller cross-sectional area is evaluated less. This means that the areal-base proportion $P^\wedge_i$ as in $P^\wedge_i=S_i/S_{all}$ for the calculation by Equation (1) increases the influences from a large cross section, and the proportion $P^\wedge_i$ will be large in classes 2 to 11 and be small in classes 1 and 12 as compared with the number-based calculation, and an error will easily occur in the determined required sample number.

This embodiment introduces the sub-classes j each including samples having a similar cross-sectional area, and calculates the required sample number $N_i$ in Equation (1) with the proportion $P^\wedge_i{}^j$ to avoid the influences from cross-sectional areas and accordingly determine a reliable required sample number for measurement.

That is, this embodiment calculates the required sample number for each class $N_i$ with the proportion $P^\wedge_i{}^j$ that is free from the influences from the cross-sectional areas, and therefore selects the temporary required sample number $N_r$, which is the maximum required sample number for each class $N_i$ among the selected classes, while making an evaluation across the sub-classes. This allows the liberation distribution to be obtained based on the number of samples while partially incorporating the concept based on the area.

Although this embodiment replaces the proportion $P^\wedge_i$ in Equation (1) with the proportion $P^\wedge_i{}^j$ that is the ratio of the number of the samples of each class i to the number of the samples belonging to each sub-class, $N_i$ and $\xi_i$ are the same as in Equation (1) as stated above, which are the values for each class i.

From the above viewpoint, the required sample-number determination device 10 determines the required sample number with the proportion $P^\wedge_i{}^j$ instead of the proportion $P^\wedge_i$ in the required sample-number determination device 1. Other operation is similar to that of the required sample-number determination device 1, and their descriptions are omitted.

A method for determining a required sample number may be implemented by the required sample-number determination device 1, 10.

Embodiment 2

Figure 6:
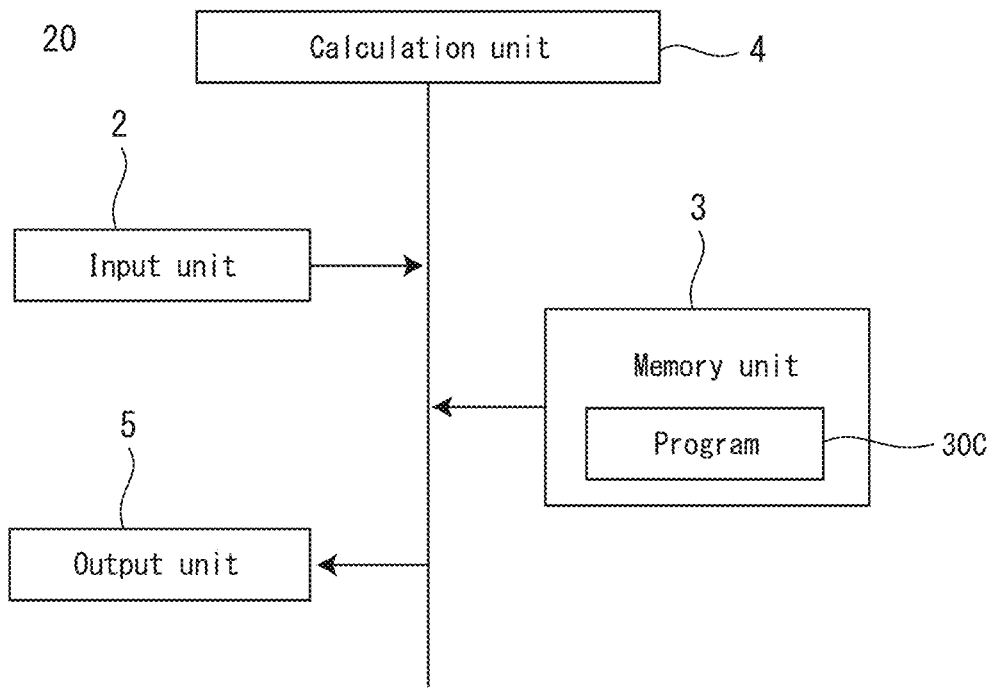
FIG. 6 is a block diagram showing the configuration of a measurement-accuracy estimation device according to Embodiment 2.

Referring to FIG. 6, the following describes the configuration of Embodiment 2 of the present invention. Embodiment 2 relates to one embodiment of a device for estimating measurement accuracy (hereinafter called a measurement-accuracy estimation device) of the present invention. FIG. 6 is a block diagram showing the configuration of the measurement-accuracy estimation device according to Embodiment 2.

As shown in FIG. 6, the measurement-accuracy estimation device 20 stores a program 30C instead of the program 30A of the required sample-number determination device 1. The following describes the operation of the measurement-accuracy estimation device 20 in accordance with the program 30C. Other configuration is similar to that of the required sample-number determination device 1, and their descriptions are omitted.

For the statistical data on the already measured physical amount, the number of measured samples also being known, the measurement-accuracy estimation device 20 estimates the accuracy ($\xi_i$) of the statistical data.

Figure 7:
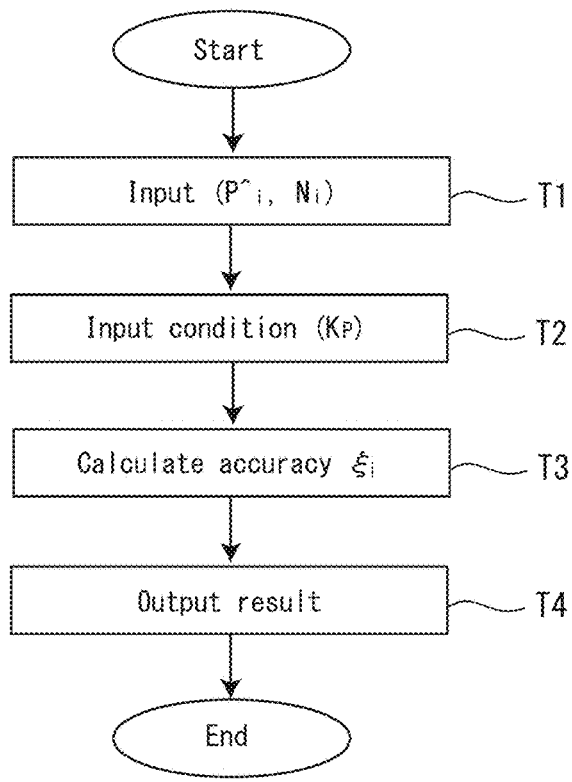
FIG. 7 is a flowchart to describe the operation of the measurement-accuracy estimation device.

Referring to FIG. 7, the following describes the operation of the measurement-accuracy estimation device 20 and the program 30C that is the program for estimating the measurement accuracy. FIG. 7 is a flowchart to describe the operation of the measurement-accuracy estimation device.

Firstly the calculation unit 4 receives information from the input unit 2 (Step T1).

When the samples of the population made up of a plurality of discrete materials are divided into a plurality of classes based on differences in the physical amount, the input information contains the proportion $P^\wedge_i$ that is the ratio of the number of the samples in each class and the number of the actually-measured samples $N_i$.

That is, when the required-number determination device 1 knows the required sample number for each class $N_i$ that is the number of the actually-measured samples $N_i$ in advance, the measurement-accuracy estimation device 20 calculates the accuracy ($\xi_i$) for the statistical data on the actual measurement.

Next the calculation unit 4 receives a condition (input) from the input unit 2 (Step T2).

The condition includes $K_P$.

Next the calculation unit 4 reads the program 30C from the memory unit 3, and executes the following processing in accordance with the program 30C.

Firstly the calculation unit 4 calculates the accuracy $\xi_i$ for each class based on the input information and the information ($N_i$, $K_P$, $P^\wedge_i$) on the conditions and through the calculation by the following Equation (1) (Step T3).

[Mathematical 8]

$$N_i = \left(\frac{K_P}{\xi_i}\right)^2 \hat{P}_i(1-\hat{P}_i) \qquad (1)$$

Next the calculation unit 4 outputs the calculated accuracy $\xi_i$ to the output unit 5 (Step T4).

This accuracy $\xi_i$ relates to whether the proportion $P_i$ satisfies the relationship of $P^\wedge_i-\xi_i<P_i<P^\wedge_i+\xi_i$ or not, where $P_i$ denotes the proportion that is the ratio of the number of the discrete materials in each class to all of the discrete materials of the population. A smaller value of $\xi_i$ indicates higher accuracy for the statistical data on the actual measurement, and a larger value of $\xi_i$ indicates lower accuracy for the statistical data on the actual measurement.

The measurement-accuracy estimation device 20 therefore estimates the accuracy for the statistical data on the actual measurement, and so ensures reliability of the statistical data on the samples of the discrete materials.

This measurement-accuracy estimation device 20 is common to the required sample-number determination devices 1 and 10 in the calculation by the above-stated Equation (1). The measurement-accuracy estimation device 20 therefore can be configured to conduct each step by the required sample-number determination devices 1 and 10 so as to execute the processing from Steps S1 to S10 and from Steps T1 to T4 in accordance with the input information and the input of setting information.

A measurement-accuracy estimation method of the present invention may be implemented by the measurement-accuracy estimation device 20.

EXAMPLES

The following verifies the advantageous effects from the required sample-number determination device according to Embodiment 1-1 and the required sample-number determination device according to Embodiment 1-2 of the present invention through a numerical experiment to measure the distribution of liberation distribution of the particles made up of two components including component A and component B as follows.

Creation of Particle Data for the Numerical Experiment

The particles were divided into 12 classes about the ratio x that indicated the ratio of component A in each particle for the distribution of the liberation distribution. These 12 classes included 0.0, more than 0.0 and 0.1 or less (0.0 to 0.1), more than 0.1 and 0.2 or less (0.1 to 0.2), ... more than 0.9 and less than 1.0 (0.9 to 1.0), and 1.0.

Figure 8:
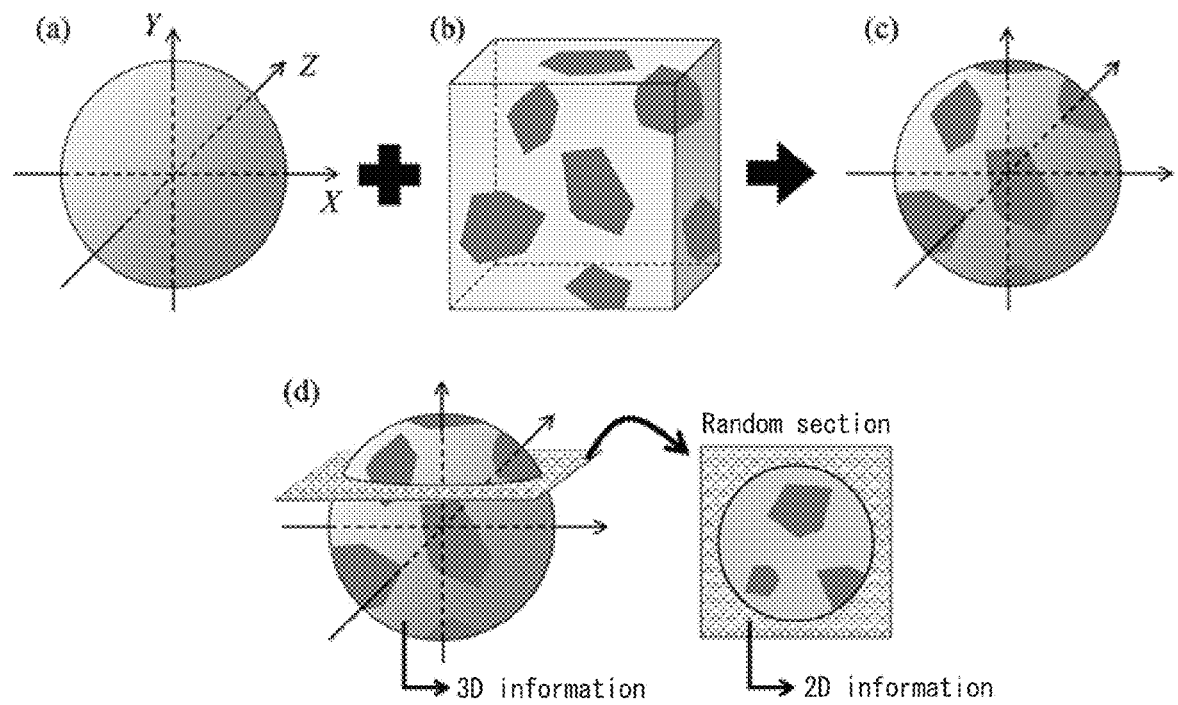
FIG. 8 describes how to create particle data used in Examples.

FIG. 8 shows the modeling procedure of such a two-component particle. FIG. 8 describes how to create particle data used in Examples.

Firstly (a) this modeling creates a spherical particle with the diameter ds.

Next (b) the modeling creates a two-component distribution of the components A and B in a certain space based on the Voronoi tessellation. The Voronoi tessellation is a technique to partition a space in which a plurality of points are present, and the partitioning is based on whether other points in the same space are close to which one of the points. Specifically the two-component distribution is created by the following procedures (1) to (3).

Firstly (1) the points in number corresponding to $V_C/V_S$ are arranged at random positions in a space. $V_C$ denotes the volume of the space. $V_S$ denotes the volume of the globe having the diameter that is the average size of the divided elements ($d_A$), i.e., the volume is given by Equation $V_S=\pi d_A^3/6$. The ratio of $d_A$ and $d_S$ is defined as the size parameter $F_S(=d_A/d_S)$.

Next (2) the Voronoi tessellation is conducted for the points.

Next (3) small elements after the tessellation are temporarily stored as component B. Randomly selected small elements are each converted into component A, and the total volume of the component A accounting for the volume of the space, i.e., the content ratio of the component A is calculated. This procedure is repeated until the content ratio exceeds a preset content ratio ($F_V$) of component A.

In this way, this modeling creates the two-component distribution including components A and B by setting two parameters of $F_S$ and $F_V$.

Next (c) the modeling combines the spherical particle and the two-component distribution to create a spherical two-component particle, and then calculates three-dimensional liberation information on the two-component particle.

Next (d) the modeling creates a cross section of the two-component particle at a random position to calculate two-dimensional liberation information in the cross section.

The modeling repeats the procedures of (a) to (d) 100,000 times to create 100,000 particles.

FIG. 10 is Table 1, which shows two types of setting values for $F_S$ and $F_V$ (particle type A and particle type B). This experiment created 100,000 particle data for each of the two types of setting values.

Figure 9:
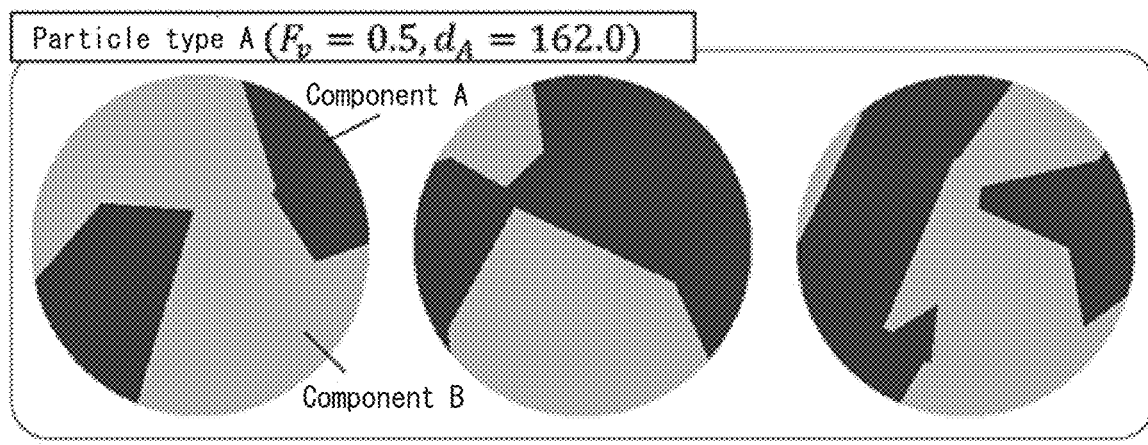
FIG. 9(*a*) shows a cross section of the particle type A.
Figure 9:
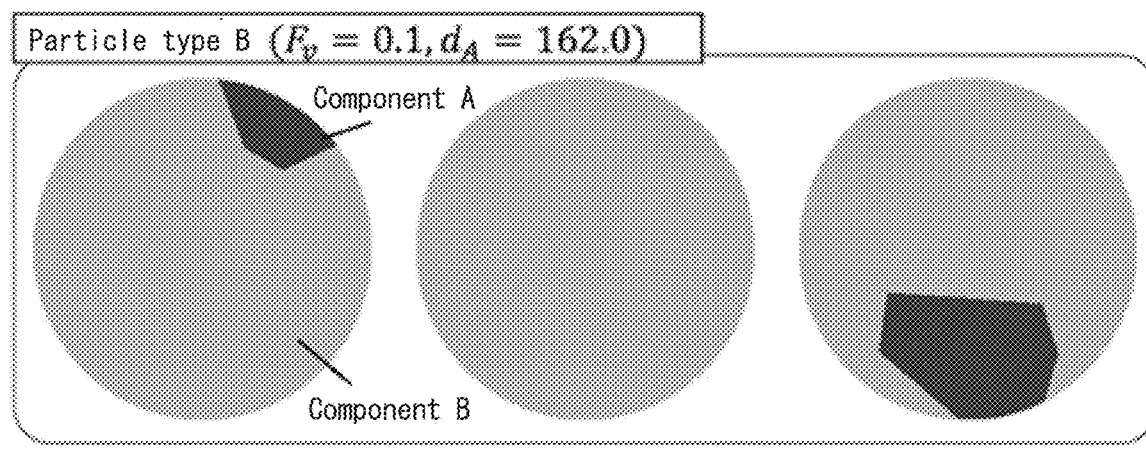

FIG. 9(a), (b) shows examples of the analyzed cross section of a spherical particle. FIG. 9(a) shows a cross section of the particle type A, and FIG. 9(b) shows a cross section of the particle type B.

Verification Method

For Step S1 of the required sample-number determination devices 1 and 10, the initial sample number $N_0$ was set at 100.

For Steps S2 to S6 of the required sample-number determination devices 1 and 10, the simplified processing was conducted for Steps S2 to S6 as described referring to FIG. 4. Note here that three types of $\xi_i$ were set for $\xi_i$ in Equation (1) as shown in FIG. 4, which were Cases 1, 2, and 3, respectively.

Case 1 set strict accuracy for all of the classes, Case 2 set strict accuracy for the class of x≥0.8, and Case 3 set strict accuracy for the classes of x=0 and x=1.

$K_P$ in Equation (1) was 1.96 by setting the reliability at 95%.

For Cases 1 to 3, three types of the liberation distribution were examined, including the liberation distribution (3D (number)) based on the three-dimensional number of samples, the liberation distribution (2D(area)) based on the number of samples while partially incorporating the concept of the two-dimensional area, and the liberation distribution (2D(number)) based on the two-dimensional number of samples.

The liberation distribution for 3D(number) and 2D(number) was verified using the required sample-number determination device 1 according to Embodiment 1-1, and the liberation distribution for 2D(area) was verified using the required sample-number determination device 10 according to Embodiment 1-2 so as to determine the required sample number for measurement ($N_r$). The term $N_r$ in this verification method refers to the true required sample number for measurement determined at Step S10.

Firstly the method calculates the distribution of liberation distribution for three types (3D(number), 2D(area), and 2D(number)) based on 100,000 particle data, where this distribution of liberation distribution is considered as the correct value. In other words, the statistical data (population statistical data) of the entire population, which would not be able to acquire, is acquired in advance by configuring the two-component particle as stated above to verify the advantageous effects of the present invention, and the data acquired is used as the correct value.

Next, the method randomly selects particle data in number corresponding to the true value of the required sample number for measurement ($N_r$) derived from the required sample-number determination devices 1, 10 from the 100,000 particle data to create three types of the distribution of liberation distribution. That is, the method acquires the statistical data (sample statistical data) containing the data on the samples in number corresponding to the required sample number for measurement $N_r$ determined by the required sample-number determination devices 1, 10.

Next the method gives a certain range, which is a correct-answer range, of the accuracy ($\pm\xi_i$) to the proportion $\hat{P}_i(\hat{P}_i^j)$ of the samples in the sample statistical data so that the proportion $\hat{P}_i(\hat{P}_i^j)$ represents the proportion ($P_i$) of the population in the population statistical data with a certain accuracy ($\pm\xi_i$) in the following Equation: $\hat{P}_i-\xi_i<P_i<\hat{P}_i+\xi_i$, and analyzes whether the proportion $\hat{P}_i(\hat{P}_i^j)$ in the sample statistical data is within the range of the correct-answer range ($\pm\xi_i$) in the relationship of $\hat{P}_i-\xi_i<P_i<\hat{P}_i+\xi_i$ or not.

The method repeats this analysis 1,000 times to calculate the probability (the percentage of correct answers (H)) of the proportion $\hat{P}_i$ in the sample statistical data being within the correct-answer range ($\pm\xi_i$).

Example 1: Particle Type A, Embodiment 1-1, 3D(Number), 2D(Number)

FIG. 11 is Table 2, which shows the required sample number for measurement $N_r$ and the percentage of correct answers R, which shows the verification result by the required sample-number determination device 1 according to Embodiment 1-1 for the particle type A, 3D(number) and 2D(number). The cells on the right of "$N_r$" indicate the required number of samples for measurement, and the cells on the right of "1" to "12" indicate the values of the percentage of correct answers R for the corresponding classes 1 to 12.

As shown in FIG. 11, the gray-colored cells in Table 2 correspond to the classes required having high accuracy.

The minimum values at the bottom in Table 2 indicate the minimum values among the total 12 classes for each measurement. These minimum values were similar to the reliability (95%) or more for the set $K_P=1.96$, and so favorable results were obtained.

Note here that for the calculation result for Case 3, 3D(number), $N_r=0$, although the initial sample number $N_0$ was set at 100, the required number of samples for measurement $N_r$ did not reach 100. Then the verification was conducted by setting $N_r=100$.

Example 2: Particle Type A, Embodiments 1-1, 1-2, 2D(Area)

The following verifies the particle type A, 2D(area) by the required sample-number determination device 1 according to Embodiment 1-1 and the required sample-number determination device 10 according to Embodiment 1-2.

FIG. 12 is Table 3, which shows $\xi_i$, the required number of samples for measurement $N_r$ for the set condition and the percentage of correct answers R for Case 1 using these devices. The required sample-number determination device 10 according to Embodiment 1-2 set $n_{size}=12$ and the sub-classes j (j are integers from 1 to 12) in accordance with the cross-sectional area. The gray-colored cells and the minimum values at the bottom are the same as those in Table 2.

While the minimum value of the required sample-number determination device 1 according to Embodiment 1-1 was 91.7%, the minimum value of the required sample-number determination device 10 that set sub-classes according to Embodiment 1-2 increased to 94.9%. This confirms the advantageous effect from the setting of the sub-classes.

Example 3: Particle Type B, Embodiment 1-1, 3D(Number), 2D(Number)

The following verifies the particle type B, 3D(number), and 2D(number) by the required sample-number determination device 1 according to Embodiment 1-1.

FIG. 13 is Table 4, which shows $\xi_i$, the required number of samples for measurement $N_r$ for the set condition and the percentage of correct answers R for Case 1. The gray-colored cells and the minimum values at the bottom are the same as those in Table 2. The minimum values in the gray-colored cells were similar to the reliability (95%) or more for the set $K_P=1.96$, and so favorable results were obtained.

Note here that for the calculation result for Case 2, 2D(number), $N_r=88$ and for Case 2, 3D(number), $N_r=0$, although the initial sample number $N_0$ was set at 100, the required number of samples for measurement $N_r$ did not reach 100. Then the verification was conducted by setting $N_r=100$.

Example 4: Particle Type B, Embodiments 1-1, 1-2, 2D(Area)

The following verifies the particle type B, 2D(area) by the required sample-number determination device 1 according to Embodiment 1-1 and the required sample-number determination device 10 according to Embodiment 1-2.

FIG. 14 is Table 5, which shows $\xi_i$, the required number of samples for measurement $N_r$ for the set condition and the percentage of correct answers R for Case 1 using these devices. The required sample-number determination device 10 according to Embodiment 1-2 set $n_{size}=12$ and the sub-classes j in accordance with the cross-sectional area. The gray-colored cells and the minimum values at the bottom are the same as those in Table 2.

While the minimum value of the required sample-number determination device 1 according to Embodiment 1-1 was 92.7%, the minimum value of the required sample-number determination device 10 according to Embodiment 1-2 that set sub-classes increased to 94.4%. This confirms the advantageous effect from the setting of the sub-classes.

DESCRIPTION OF REFERENCE NUMERALS

1, 10 Required sample-number determination device
2 Input unit
3 Memory unit
4 Calculation unit
5 Input unit
20 Measurement-accuracy estimation device
30A, 30B, 30C Program

The invention claimed is:

1. An information processing apparatus, comprising:
a memory; and
a processor coupled to the memory and configured to:
calculate, for each selected class i among a plurality of classes, a number Ni, which represents a number of required samples, from a ratio $\hat{P}_i$ of a number of samples in the selected class to a number of all samples $N_0$, an accuracy $\xi_i$ of the selected class and a constant Kp associated with a confidence level, according to an equation $$N_i = \left(\frac{K_P}{\xi_i}\right)^2 \hat{P}_i(1 - \hat{P}_i), \quad (1)$$

wherein the plurality of classes are obtained by classifying a plurality of discrete materials that are samples extracted from a population based on a physical amount for each of the plurality of discrete materials, the confidence level is set as a probability that satisfies $\hat{P}_i - \xi_i < P_i < \hat{P}_i + \xi_i$, and Pi is a ratio of a number of discrete materials in the selected class to a number of all discrete materials in the population;

specify a temporarily required sample number Nr that is a maximum number among numbers Ni calculated for respective selected classes; and repeat the calculating and the specifying with a new ratio P^i of a number of new samples in the each selected class i to a number of all new samples $N_0$ that is equal to or greater than the temporarily required sample number Nr until a condition that the number of all new samples $N_0$ becomes equal to or greater than a new temporarily required sample number Nr specified among new numbers Ni or a predetermined exceptional condition is satisfied, wherein the new samples are extracted from the population.

2. The information processing apparatus as set forth in claim 1, wherein the discrete materials are multicomponent particles, and the physical amount is a degree of liberation of the multicomponent particles.

3. The information processing apparatus as set forth in claim 1, wherein the physical amount includes a first physical amount and a second physical amount, and the plurality of classes are made based on the first physical amount and each of the plurality of classes is divided into a plurality of subclasses based on the second physical amount, and the number Ni is calculated by using, as the ratio P^i, a ratio P^ij of a number of samples in a selected subclass j of a plurality of subclasses included in a certain class i to a number of samples in the certain class i of the plurality of classes.

4. A non-transitory, computer-readable storage medium storing a program for causing a computer to execute a process comprising:

calculating, for each selected class i among a plurality of classes, a number Ni, which represents a number of required samples, from a ratio P^i of a number of samples in the selected class to a number of all samples $N_0$, an accuracy $\xi_i$ of the selected class and a constant Kp associated with a confidence level, according to an equation $$N_i = \left(\frac{K_P}{\xi_i}\right)^2 \hat{P}_i(1 - \hat{P}_i), \quad (1)$$

wherein the plurality of classes are obtained by classifying a plurality of discrete materials that are samples extracted from a population based on a physical amount for each of the plurality of discrete materials, the confidence level is set as a probability that satisfies $\hat{P}_i - \xi_i < P_i < \hat{P}_i + \xi_i$, and Pi is a ratio of a number of discrete materials in the selected class to a number of all discrete materials in the population;

specifying a temporarily required sample number Nr that is a maximum number among numbers Ni calculated for respective selected classes; and repeating the calculating and the specifying with a new ratio P^i of a number of new samples in the each selected class i to a number of all new samples $N_0$ that is equal to or greater than the temporarily required sample number Nr until a condition that the number of all new samples $N_0$ becomes equal to or greater than a new temporarily required sample number Nr specified among new numbers Ni or a predetermined exceptional condition is satisfied, wherein the new samples are extracted from the population.

5. An information processing method, comprising:

calculating, by using a computer, for each selected class i among a plurality of classes, a number Ni, which represents a number of required samples, from a ratio P^i of a number of samples in the selected class to a number of all samples $N_0$, an accuracy $\xi_i$ of the selected class and a constant Kp associated with a confidence level, according to an equation $$N_i = \left(\frac{K_P}{\xi_i}\right)^2 \hat{P}_i(1 - \hat{P}_i), \quad (1)$$

wherein the plurality of classes are obtained by classifying a plurality of discrete materials that are samples extracted from a population based on a physical amount for each of the plurality of discrete materials, the confidence level is set as a probability that satisfies $\hat{P}_i - \xi_i < P_i < \hat{P}_i + \xi_i$, and Pi is a ratio of a number of discrete materials in the selected class to a number of all discrete materials in the population;

specifying, by using the computer, a temporarily required sample number Nr that is a maximum number among numbers Ni calculated for respective selected classes; and repeating, by using the computer, the calculating and the specifying with a new ratio P^i of a number of new samples in the each selected class i to a number of all new samples $N_0$ that is equal to or greater than the temporarily required sample number Nr until a condition that the number of all new samples $N_0$ becomes equal to or greater than a new temporarily required sample number Nr specified among new numbers Ni or a predetermined exceptional condition is satisfied, wherein the new samples are extracted from the population.

* * * * *